United States Patent
Orr et al.

(10) Patent No.: US 9,827,111 B2
(45) Date of Patent: Nov. 28, 2017

(54) ARTHROSCOPIC TISSUE SCAFFOLD DELIVERY DEVICE

(71) Applicant: DePuy Mitek, LLC, Raynham, MA (US)

(72) Inventors: Keith M. Orr, Boston, MA (US); Eric Hyman, Ashland, MA (US); Francois Binette, San Francisco, CA (US); Ian D. McRury, Medway, MA (US); Steve Lepke, Wakefield, MA (US); Ash Perkins, Natick, MA (US); Julia Hwang, Wayland, MA (US)

(73) Assignee: DEPUY MITEK, LLC, Raynham, MA (US)

( * ) Notice: Subject to any disclaimer, the term of this patent is extended or adjusted under 35 U.S.C. 154(b) by 482 days.

(21) Appl. No.: 14/179,973

(22) Filed: Feb. 13, 2014

(65) Prior Publication Data
US 2014/0163695 A1 Jun. 12, 2014

Related U.S. Application Data

(63) Continuation of application No. 10/724,021, filed on Nov. 26, 2003, now Pat. No. 8,673,021.

(51) Int. Cl.
*A61F 2/46* (2006.01)
*A61B 17/00* (2006.01)
(Continued)

(52) U.S. Cl.
CPC .......... *A61F 2/46* (2013.01); *A61B 17/00234* (2013.01); *A61B 2017/00575* (2013.01);
(Continued)

(58) Field of Classification Search
CPC ............. A61F 2/46; A61B 2017/00575; A61B 2017/1205
(Continued)

(56) References Cited

U.S. PATENT DOCUMENTS 3,570,485 A * 3/1971 Reilly ............... A61M 25/0668
604/164.11
3,581,956 A 6/1971 Reid
(Continued)

FOREIGN PATENT DOCUMENTS

| JP | 11-347057 A | 12/1999 |
| JP | 2001-129003 A | 5/2001 |
| JP | 2001-286478 A | 10/2001 |

OTHER PUBLICATIONS

European Office Action for Application No. 04257325.3 dated Jan. 3, 2017 (4 Pages).
Japan O.A. #2004340867, dated Jun. 8, 2010.

*Primary Examiner* — Dianne Dornbusch

(57) ABSTRACT

A small diameter delivery device capable of delivering a tissue loaded scaffold arthroscopically to a tissue defect or injury site without reducing the pressure at the injury site is provided. The scaffold delivery device of the present invention comprises a plunger system that includes two main components: an insertion tube and an insertion rod. The insertion tube has a flared proximal end for holding a tissue scaffold prior to delivery. An elongate, hollow body extends from the flared proximal end to a distal end of the insertion tube, and defines a passageway that extends through the body for delivery of the tissue scaffold. The insertion rod has an elongate body that extends into a handle at a proximal end and a tip at a distal end. The insertion rod is configured to be removably disposed within the insertion tube for sliding along the passageway to effect delivery of the tissue scaffold through the insertion tube.

22 Claims, 2 Drawing Sheets

(51) Int. Cl.
  *A61B 17/12* (2006.01)
  *A61F 2/30* (2006.01)
  *A61F 2/40* (2006.01)

(52) U.S. Cl.
  CPC ......... *A61B 2017/1205* (2013.01); *A61F 2002/30281* (2013.01); *A61F 2002/30426* (2013.01); *A61F 2002/30604* (2013.01); *A61F 2002/30772* (2013.01); *A61F 2002/30878* (2013.01); *A61F 2002/30881* (2013.01); *A61F 2002/30897* (2013.01); *A61F 2002/4022* (2013.01); *A61F 2002/4085* (2013.01)

(58) Field of Classification Search
  USPC ......... 606/108; 604/164.09, 164.1, 164.12, 604/164.13, 232, 164.11; 600/184
  See application file for complete search history.

(56) References Cited

U.S. PATENT DOCUMENTS

| | | | |
|---|---|---|---|
| 3,900,954 A | 8/1975 | Dragan | |
| 3,955,719 A * | 5/1976 | Pheulpin | A61C 5/04 222/386 |
| 4,173,227 A * | 11/1979 | Cassou | A61D 19/027 604/218 |
| 4,232,670 A * | 11/1980 | Richter | A61B 17/8802 604/218 |
| 4,335,730 A * | 6/1982 | Griffin | A61B 10/007 141/331 |
| 4,373,535 A | 2/1983 | Martell | |
| 4,411,655 A * | 10/1983 | Schreck | A61M 25/0662 285/381.2 |
| 4,472,141 A | 9/1984 | Dragan | |
| 4,492,576 A | 1/1985 | Dragan | |
| 4,623,336 A * | 11/1986 | Pedicano | A61M 5/002 604/110 |
| 4,655,749 A | 4/1987 | Fischione | |
| 4,670,008 A * | 6/1987 | Von Albertini | A61M 25/0606 604/165.01 |
| 4,790,819 A | 12/1988 | Li et al. | |
| 4,852,584 A * | 8/1989 | Selby | B01L 3/00 600/573 |
| 4,863,072 A | 9/1989 | Perler | |
| 5,053,010 A | 10/1991 | McGary et al. | |
| 5,125,898 A | 6/1992 | Kaufhold, Jr. et al. | |
| 5,176,649 A | 1/1993 | Wakabayashi | |
| 5,188,599 A | 2/1993 | Botich et al. | |
| 5,221,348 A | 6/1993 | Masano | |
| 5,244,122 A * | 9/1993 | Botts | A61J 7/0046 222/158 |
| 5,284,480 A | 2/1994 | Porter et al. | |
| 5,324,273 A | 6/1994 | Discko, Jr. | |
| 5,401,246 A | 3/1995 | Mazur et al. | |
| 5,413,564 A | 5/1995 | Silver et al. | |
| 5,549,573 A | 8/1996 | Waskonig | |
| 5,622,498 A * | 4/1997 | Brizzolara | A61C 19/063 433/80 |
| 5,685,857 A | 11/1997 | Negus et al. | |
| 5,690,674 A | 11/1997 | Diaz | |
| 5,697,932 A | 12/1997 | Smith et al. | |
| 5,733,950 A | 3/1998 | Dunn et al. | |
| 5,814,073 A * | 9/1998 | Bonutti | A61B 17/0401 604/14 |
| 5,817,066 A | 10/1998 | Goforth | |
| 5,827,319 A * | 10/1998 | Carlson | A61B 17/3439 604/264 |
| 5,957,902 A | 9/1999 | Teves | |
| 5,997,515 A | 12/1999 | de la Torre et al. | |
| 6,004,303 A * | 12/1999 | Peterson | A61B 17/3439 604/167.01 |
| 6,019,765 A | 2/2000 | Thornhill et al. | |
| 6,328,715 B1 * | 12/2001 | Dragan | A23G 9/24 604/232 |
| 6,447,489 B1 * | 9/2002 | Peterson | A61B 17/3439 600/204 |
| 6,461,631 B1 | 10/2002 | Dunn et al. | |
| 6,589,225 B2 | 7/2003 | Orth et al. | |
| 6,592,555 B1 | 7/2003 | Wen-Pi et al. | |
| 6,613,074 B1 | 9/2003 | Mitelberg et al. | |
| 6,656,496 B1 | 12/2003 | Kilpadi et al. | |
| 6,793,660 B2 | 9/2004 | Kerr et al. | |
| 6,884,428 B2 | 4/2005 | Binette et al. | |
| 6,932,804 B2 | 8/2005 | Lee | |
| 7,166,133 B2 | 1/2007 | Evans et al. | |
| D545,429 S | 6/2007 | Hays | |
| 7,388,657 B2 | 6/2008 | Abbott | |
| 7,572,263 B2 | 8/2009 | Preissman | |
| 7,727,542 B2 | 6/2010 | DiBenedetto et al. | |
| 2002/0002360 A1 | 1/2002 | Orth et al. | |
| 2002/0151974 A1 | 10/2002 | Bonassar et al. | |
| 2003/0073979 A1 | 4/2003 | Naimark et al. | |
| 2003/0195477 A1 | 10/2003 | Ruben | |
| 2003/0216669 A1 | 11/2003 | Lang et al. | |
| 2004/0002740 A1 | 1/2004 | Lee | |
| 2004/0030345 A1 | 2/2004 | Aurin et al. | |
| 2004/0049203 A1 * | 3/2004 | Scribner | A61B 17/1631 606/93 |
| 2004/0204715 A1 | 10/2004 | Evans et al. | |
| 2004/0234571 A1 | 11/2004 | Jang | |
| 2004/0267277 A1 * | 12/2004 | Zannis | A61F 2/4618 606/99 |
| 2005/0079470 A1 | 4/2005 | Rutherford et al. | |
| 2005/0113736 A1 | 5/2005 | Orr et al. | |

* cited by examiner

ARTHROSCOPIC TISSUE SCAFFOLD DELIVERY DEVICE

FIELD OF THE INVENTION

This application is a continuation of U.S. application Ser. No. 10/724,021, filed Nov. 26, 2003, now U.S. Pat. No. 8,673,021, the contents of which are hereby incorporated by reference in its entirety.

BACKGROUND

Injuries to soft tissue, such as cartilage, skin, muscle, bone, tendon, and ligament where the tissue has been injured or traumatized frequently require surgical intervention to repair the damage and facilitate healing. Such surgical repairs can include suturing or otherwise repairing the damaged tissue with known medical devices, augmenting the damaged tissue with other tissue, using an implant, a graft or any combination of these techniques.

One common technique for repairing diseased or injured tissue is to implant a tissue scaffold at the defect site, either alone or along with cultured and amplified cells. In the past, such scaffolds have consisted mostly of two- or three-dimensional porous scaffolds that allow cell invasion and remodeling once the scaffold has been combined with living cells and has been delivered inside the patient. Another technique is to load the tissue scaffolds with tissue fragments and then implanting the tissue-laden scaffold at the defect site. Depending where the defect is located and the size of the defect, these tissue loaded scaffolds can vary from a few millimeters to several dozen millimeters in length and width.

The current method for implanting these tissue scaffolds is by an open or mini-open surgical procedure, which increases recovery time for the patient. Although a fully arthroscopic procedure for delivering a tissue-loaded scaffold to a defect site would be advantageous because of its minimally invasive nature and reduced side effects, there is presently no convenient method for delivering the tissue-loaded scaffolds through a cannula to the defect site without the risk of damaging the scaffold in the process. Moreover, where it is necessary to deliver the scaffold to a defect in a joint, there is currently no acceptable way to arthroscopically deliver the scaffold without reducing the pressure inside the joint. It would therefore be desirable to provide a method and device which allows delivery of a tissue loaded scaffold in a fully arthroscopic procedure. It would also be advantageous to provide a delivery device which allows the scaffold to be delivered through a small diameter tube to a defect in a joint without reducing the pressure inside the joint.

SUMMARY OF THE INVENTION

The present invention provides a small diameter delivery device capable of delivering a tissue loaded scaffold arthroscopically to a tissue defect or injury site without reducing the pressure at the injury site. The scaffold delivery device of the present invention comprises a plunger system that includes two main components: an insertion tube and an insertion rod. The first component, the insertion tube, is configured with a flared proximal end for holding a tissue scaffold prior to delivery. An elongate, hollow body extends from the flared proximal end to a distal end of the insertion tube. The elongate, hollow body defines a passageway that extends through the body for delivery of the tissue scaffold. The second component, the insertion rod, comprises an elongate body that extends into a handle at a proximal end and a tip at a distal end. The insertion rod is configured to be removably disposed within the insertion tube for sliding along the passageway to effect delivery of the tissue scaffold through the insertion tube.

The passageway of the hollow, elongate body includes a first, flared portion that gradually extends into a second, tubular portion. Prior to delivery, the tissue scaffold can be held inside the insertion tube at the first, flared portion until the insertion rod is placed on the scaffold and urged distally. The force of the tip of the insertion rod against the tissue scaffold moves the scaffold through the passageway and out the distal end of the insertion tube. The gradual taper of the passageway allows the implant to be delivered without incurring damage in the process. Due to the small diameter of the insertion tube, the tissue scaffold can be arthroscopically delivered without reducing the pressure at the implantation site.

BRIEF DESCRIPTION OF THE DRAWINGS

The invention can be more fully understood from the following detailed description taken in conjunction with the accompanying exemplary drawing, in which.

DETAILED DESCRIPTION OF THE INVENTION

Figure 1:
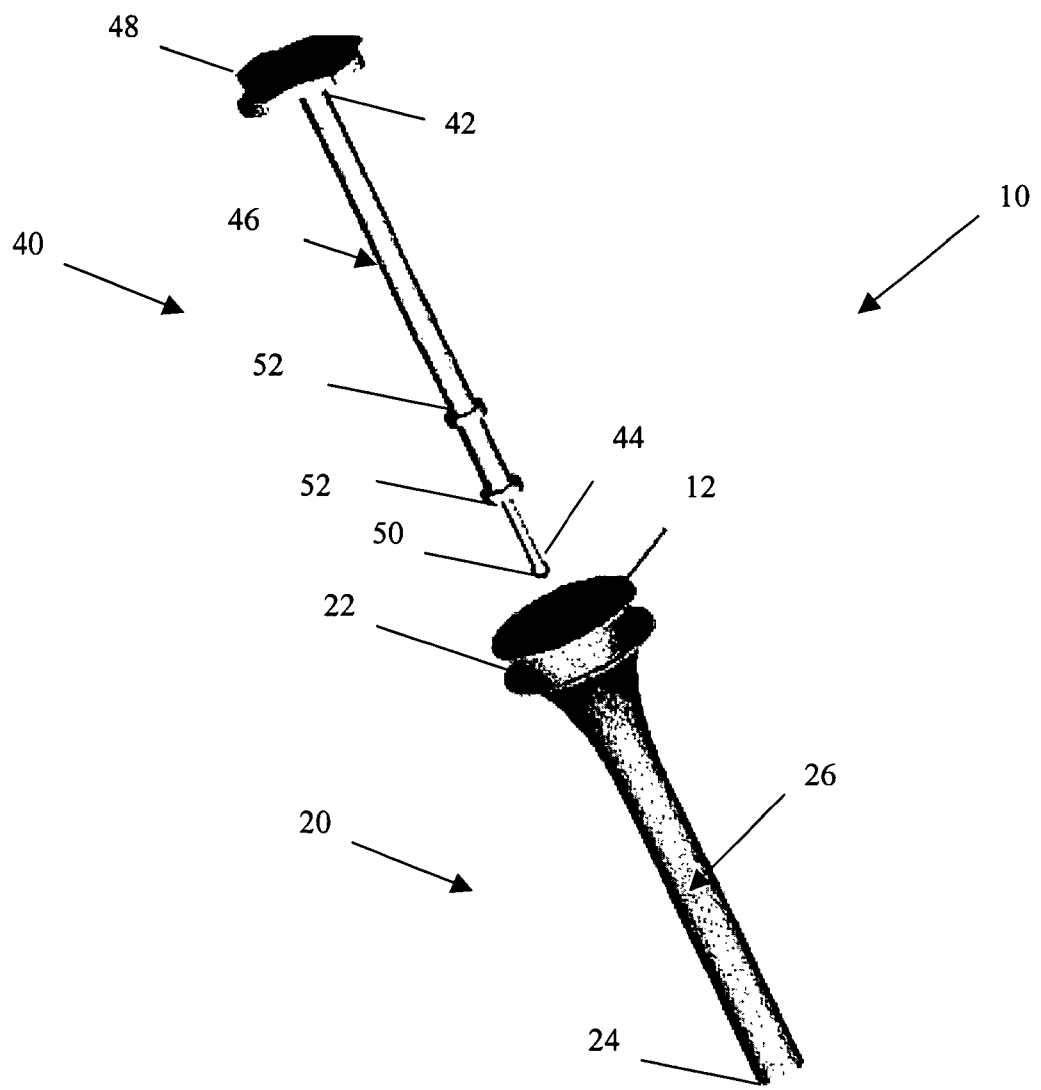
FIG. 1 illustrates an exploded view of the delivery device of the present invention.
Figure 2A:
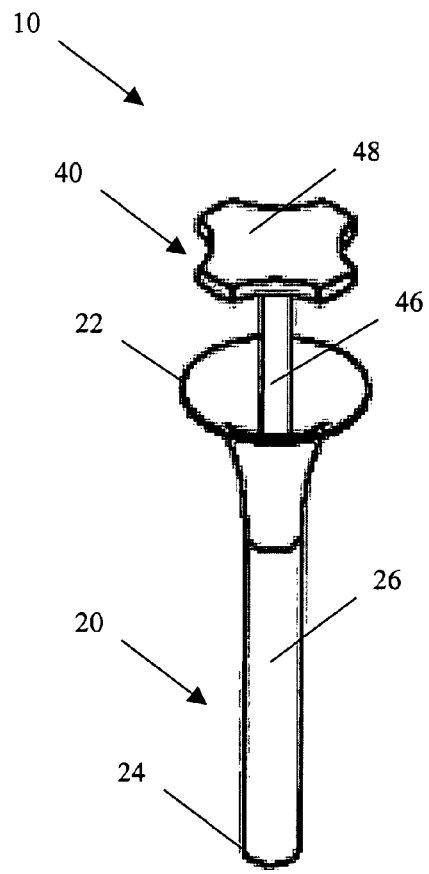
FIG. 2A illustrates a perspective view of the delivery device of FIG. 1.
Figure 2B:
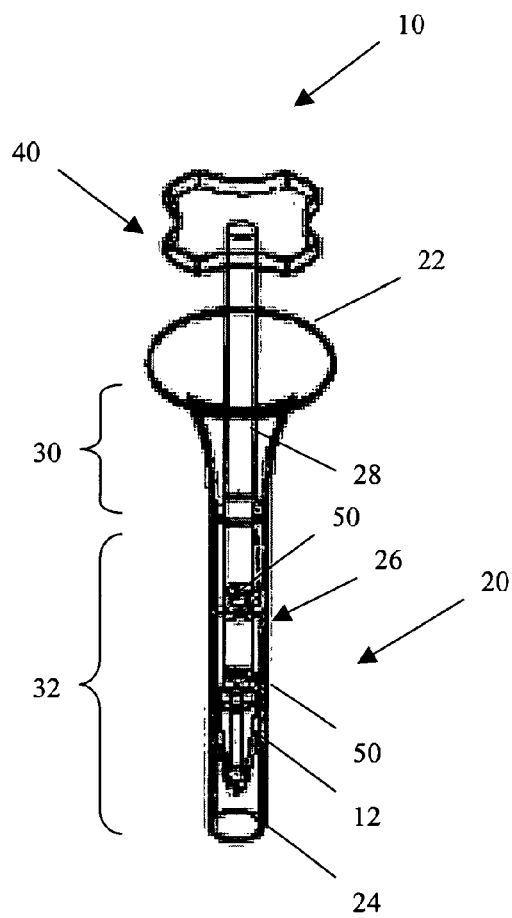
FIG. 2B is a cutaway view of the delivery device of FIG. 2A.

Turning now to the drawings and particularly to FIG. 1, a delivery system 10 for delivering a tissue scaffold 12 in accordance with the present invention is shown. The delivery system 10 comprises two main components. The first component is an insertion tube 20 and the second component is an insertion rod 40. The insertion tube 20 is defined by a flared proximal end 22 and a distal end 24. Extending between these ends 22, 24 is a hollow, elongate body 26. As shown in FIG. 2B, the hollow, elongate body 26 defines a passageway 28 comprising a first, flared portion 30 that extends into a second, tubular portion 32. The first, flared portion 30 can have a curved taper in order to provide a smooth transition between the two portions 30, 32 and to avoid damage to the tissue scaffold 12 during its delivery. The first, flared portion 30 can be integral with the second, tubular portion 32. Alternatively, the first, flared portion 30 can be provided as a separate component which is then attached to the second, tubular portion 32 to collectively form the insertion tube 20.

The second component of the delivery system 10, the insertion rod 40, comprises an elongate shaft 46 that extends into a handle 48 at a proximal end and a tip 50 at a distal end. As shown, the handle 48 is configured as a contoured grip for ease of handling. It is understood, however, that the handle 48 can comprise other configurations having any shape or size appropriate for the purposes of this invention. Meanwhile, the tip 50 can be blunt, having a spherical shape as illustrated in FIG. 1 for preventing damage to the tissue scaffold 12 during the delivery. The elongate shaft 46 is configured to be removably disposed within the insertion tube 20 for sliding along the passageway 28. Sealing rings 52 can be placed on the elongate shaft 46 to help align the insertion rod 40 and prevent backflow of fluid through the insertion tube 20 during the delivery process. These sealing rings 52 can be made from a softer material than the insertion rod 40, and can be provided as separate components for adjustable placement on the insertion rod 40.

In one aspect of the present invention, the flared proximal end 22 of the insertion tube 20 has a diameter in the range of about 15 mm to about 50 mm to accommodate a variety of sized and shaped tissue scaffolds 12 known in the art. The passageway 28 of the insertion tube 20 can have a second tubular portion 32 with a diameter in the range of about 6 mm to about 17 mm, preferably about 7 mm to about 9 mm. The spherical tip 50 can have a diameter in the range of about 6 mm to about 10 mm, preferably about 6 mm to about 8 mm. These small dimensions ensure not only that the scaffold delivery can be accomplished in a fully arthroscopic procedure, but that damage to the tissue scaffold 12 during the delivery process can be minimized. In addition, the maximum outer diameter of the elongate shaft 26, including the sealing ring 52, should approximate the diameter of the second tubular portion 32, so that backflow of fluid can be prevented and so that a closed volume within the insertion tube 20 can be attained when the insertion rod 40 is disposed within the passageway 28.

The delivery system 10 can be formed from any suitable biocompatible metal or polymer. For example, the delivery system 10 can be formed from a medical grade surgical steel, or the delivery system 10 can be formed from a sterilizable, medical grade plastic such as polycarbonate. The sealing rings 52 of the insertion rod 40 can be formed from a compliant material such as silicone. It should be understood that the present invention is not to be limited to these materials, and one skilled in the art would recognize that the delivery system 10 of the present invention can be made from a variety of other suitable materials.

The delivery system 10 of the present invention works in a plunger-like manner. In use, a patient having a damaged or diseased tissue site is prepared for arthroscopic surgery. With the insertion rod 40 separate from the insertion tube 20, a tissue scaffold 12 can be loaded into the delivery system 10 by placing the scaffold 12 within the flared portion of the passageway 28. Depending on the dimensions and shape of the scaffold 12, the scaffold 12 can be slightly folded or rolled into a configuration similar to the one illustrated in FIG. 1. The first, flared portion 30 of the passageway 28 should be configured to sufficiently allow the scaffold 12 to seat within the insertion tube 20 at the flared, proximal end 22 without too much friction.

Next, the insertion rod 40 is placed onto the tissue scaffold 12, with the tip 50 contacting the tissue scaffold 12. Applying pressure against the handle 48, the insertion rod 40 is urged down the passageway 28 of the insertion tube 20, thus sliding the tissue scaffold 12 along with the depressed rod 40 into the insertion tube 20. The tissue scaffold 12 can be slid down the second tubular portion 32 of the passageway 28 until the tissue scaffold 12 almost reaches the distal end 24 of the insertion tube. The sealing rings 52 on the elongate shaft 46 of the insertion rod 40 help align the rod 40 inside the insertion tube 20 so that the movement of the insertion rod 40 and tissue scaffold 12 run parallel to the length of the insertion tube 20. In addition, the sealing rings also serve to prevent backflow of fluid up through the insertion tube and to maintain a closed volume between the delivery device 10 and the implant site during the delivery process.

When the surgeon is ready to deliver the tissue scaffold 12 to the damaged or injured tissue site, the insertion tube 20 along with the tissue scaffold 12 can then be inserted directly through the incision and positioned so that the distal end 24 is located where the scaffold 12 is to be delivered. The surgeon would then continue depressing the insertion rod 40 until the tissue scaffold 12 is fully exposed to the implant site. After the tissue scaffold 12 exits the distal end 24 of the insertion tube, the insertion rod 40 can be removed and the delivery system 10 can be discarded, or it can be reused if desired. Because of the small size of the delivery system 10, it is understood that the entire delivery process can be accomplished in a fully arthroscopic procedure.

The delivery system 10 of the present invention is configured to accommodate tissue scaffolds 12 of various sizes and shapes known in the art. Where the tissue scaffold 12 also requires an adhesive or glue component for securing the scaffold 12 to the tissue defect or injury, the tissue scaffold 12 along with the glue component can be loaded into the insertion tube 20, preferably with the glue component on the inside, facing towards the passageway 28. Where it is desirable to use a fixation device such as a staple or tack to secure the scaffold 12, it is contemplated that the tissue scaffold 12 can be loaded with the fixation device extending at least partially through the tissue scaffold 12. The scaffold 12 can be position within the first flared portion 30 such that the fixation device is exposed. Then, the insertion rod 40 can be depressed against the fixation device to deliver both the tissue scaffold 12 along with the fixation device to the site of implantation. In another embodiment, the insertion rod 40 can have a tip 50 which is configured (not shown) to attach to or mate with the fixation device, thereby allowing greater control over the delivery of the scaffold 12. Also, where the tissue scaffold 12 has a unique geometry, it is contemplated that the tip 50 can be formed as a piercing tip (not shown) in order to hold the scaffold 12 in place during the delivery process.

In yet another embodiment, the insertion rod 40 and the insertion tube 20 can be connected by a trigger mechanism (not shown) similar to the depression mechanism of a caulk gun. The trigger mechanism can include a handle or grip with an attached pivoting trigger. The handle or grip can be fixedly attached to the insertion tube 20, while the trigger can be attached to the insertion rod 40. By depressing the trigger either forwards or backwards, the insertion rod 40 can be retract away from the proximal end 22 of the insertion tube 20 to enable a tissue scaffold 12 to be loaded, or advanced towards the distal end 24 of the insertion tube 20 to effect movement of the scaffold 12 through the distal end 24. It is contemplated that the configuration of the insertion tube 20 and insertion rod 40 (including the sealing rings 52) would be similar to the ones previously described. This trigger mechanism would provide the surgeon with greater control over the advancement of the scaffold 12, and better ensure the alignment of the insertion rod 40 with respect to the insertion tube 20.

It will be understood that the foregoing is only illustrative of the principles of the invention, and that various modifications can be made by those skilled in the art without departing from the scope and spirit of the invention.

The invention claimed is:

1. A method for delivering a tissue scaffold to an injured or defective tissue, comprising the steps of:
    positioning a tissue scaffold at a flared proximal end of an insertion tube of a delivery system, the flared proximal end having a first inner diameter, the insertion tube having an elongate portion extending distally from the flared proximal end, the insertion tube having a distal end and a passageway extending between the distal end and the flared proximal end, the passageway having a second inner diameter that is smaller than the first inner diameter, and the delivery system comprising an insertion rod having an elongate shaft extending into a handle at a proximal end of the insertion rod and a blunt tip at a distal end of the insertion rod, the elongate shaft being configured to be removably disposed within the insertion tube for sliding along the passageway; and placing the insertion rod into contact with the tissue scaffold that is positioned at the flared proximal end of the insertion tube and depressing the insertion rod to thereby cause the tissue scaffold to enter the elongate portion of the insertion tube and advance toward the distal end of the insertion tube until the tissue scaffold exits the distal end of the insertion tube within a body of a patient.

2. The method of claim 1, wherein the steps are performed arthroscopically.

3. The method of claim 1, wherein depressing the insertion rod includes sliding the insertion rod distally along the passageway of the insertion tube.

4. The method of claim 3, wherein the insertion rod includes a sealing member on the elongate shaft, the sealing member providing a fluid seal in the passageway during the sliding of the insertion rod along the passageway.

5. The method of claim 3, wherein the insertion rod includes an alignment member on the elongate shaft, the alignment member aligning the elongate shaft with the passageway such that the elongate shaft is slid parallel to a longitudinal axis of the passageway.

6. The method of claim 5, wherein the alignment member provides a fluid seal in the passageway during the sliding of the insertion rod along the passageway.

7. The method of claim 1, wherein depressing the insertion rod includes depressing a blunt tip at the distal end of the insertion rod.

8. The method of claim 1, wherein the insertion rod is a separate element from the insertion tube and is separated from the insertion tube when the tissue scaffold is positioned at the flared proximal end of the insertion tube.

9. The method of claim 1, further comprising, after the tissue scaffold is positioned at the flared proximal end, advancing the insertion tube, the tissue scaffold, and the insertion rod as a unit into the body of the patient.

10. The method of claim 1, wherein depressing the insertion rod against the tissue scaffold includes a first step, in which the tissue scaffold is advanced distally along the passageway toward the distal end of the insertion tube to a position where the tissue scaffold is contained within the passageway, and a second step, in which the tissue scaffold is advanced distally from the position to exit the distal end of the insertion tube; and
wherein the first step occurs with the insertion tube outside the body of the patient, and the second step occurs with the insertion tube within the body of the patient.

11. The method of claim 1, wherein the tissue scaffold is positioned at the flared proximal end with the insertion tube entirely outside the body of the patient.

12. The method of claim 1, wherein the tissue scaffold is a planar member.

13. The method of claim 1, wherein depressing the insertion rod to thereby cause the tissue scaffold to enter the elongate portion of the insertion tube also causes the tissue scaffold to deform in shape.

14. The method of claim 1, wherein placing the insertion rod into contact with the tissue scaffold includes placing a distal tip of the insertion rod into contact with the tissue scaffold, the insertion rod has a sealing member thereon at a location that is proximal to a distal tip of the insertion rod, and the sealing member provides a fluid seal in the passageway during the depressing of the insertion rod and the advancement of the tissue scaffold toward the distal end of the insertion tube.

15. The method of claim 14, wherein the insertion rod is formed of a rigid material, and the sealing member is formed of a compliant material.

16. A surgical method, comprising:
introducing a tissue scaffold into a first opening in a proximal end of an elongate tube, the first opening in the proximal end of the elongate tube having a first diameter, a second opening in a distal end of the elongate tube having a second diameter that is less than the first diameter, and the elongate tube having a passageway extending between the first and second openings;

after introducing the tissue scaffold into the first opening of the elongate tube, introducing a distal portion of an elongate insertion member into the first opening of the elongate tube and thereby causing initial contact between the distal portion of the elongate insertion member and the tissue scaffold, and moving the distal portion of the elongate insertion member in a distal direction through the passageway and thereby moving the tissue scaffold through the passageway in the distal direction until the tissue scaffold is within the passageway at a location that is proximal to the distal end of the elongate tube;

positioning the distal end of the elongate insertion member adjacent a target tissue site within a patient; and further moving the distal portion of the elongate insertion member in the distal direction through the passageway and thereby moving the tissue scaffold through the passageway in the distal direction from the location until the tissue scaffold passes out of the elongate tube through the second opening to the target tissue site;

wherein the insertion rod has a sealing member thereon at a location that is proximal to a blunt distal tip of the insertion rod that presses on the tissue scaffold during the movement of the distal portion of the elongate insertion member in the distal direction through the passageway, and the sealing member forms a fluid seal in the passageway during the movement of the distal portion of the elongate insertion member in the distal direction through the passageway.

17. The method of claim 16, wherein moving the distal portion of the elongate insertion member includes a distal tip of the elongate insertion member pushing distally on the tissue scaffold.

18. The method of claim 16, wherein a proximal longitudinal length of the elongate tube gradually tapers from the first diameter to the second diameter, and a distal longitudinal length of the elongate tube has the second diameter.

19. The method of claim 16, wherein the distal end of the elongate insertion member is not positioned adjacent the target tissue site until after the tissue scaffold has been moved to the location.

20. The method of claim 16, further comprising, after the tissue scaffold has been introduced into the first opening of the elongate tube and before further moving the distal portion of the elongate insertion member in the distal direction through the passageway and thereby moving the tissue scaffold through the passageway in the distal direction from the location, introducing the elongate tube into the patient.

21. The method of claim 16, further comprising, after the tissue scaffold is within the passageway at the location and before further moving the distal portion of the elongate insertion member in the distal direction through the passageway and thereby moving the tissue scaffold through the passageway in the distal direction from the location, introducing the elongate tube into the patient.

22. The method of claim 16, wherein the tissue scaffold is a planar member.

* * * * *